(12) United States Patent
Carlucci et al.

(10) Patent No.: US 8,581,019 B2
(45) Date of Patent: *Nov. 12, 2013

(54) ABSORBENT ARTICLE HAVING INCREASED ABSORPTION AND RETENTION CAPACITY FOR PROTEINACEOUS OR SEROUS BODY FLUIDS

(75) Inventors: Giovanni Carlucci, Chieti (IT); Alessandro Gagliardini, Villa Vomano (IT)

(73) Assignee: The Procter and Gamble Company, Cincinnati, OH (US)

( * ) Notice: Subject to any disclaimer, the term of this patent is extended or adjusted under 35 U.S.C. 154(b) by 598 days.

This patent is subject to a terminal disclaimer.

(21) Appl. No.: 11/584,101

(22) Filed: Oct. 20, 2006

(65) Prior Publication Data

US 2008/0091159 A1    Apr. 17, 2008

(30) Foreign Application Priority Data

Oct. 21, 2005 (EP) ..................................... 05023061

(51) Int. Cl.
*A61F 13/15* (2006.01)
*A61F 13/20* (2006.01)

(52) U.S. Cl.
USPC ..................................... 604/367; 604/385.01

(58) Field of Classification Search
USPC .......... 604/358, 385.01, 385.22–385.24, 367, 604/375, 378
See application file for complete search history.

(56) References Cited

U.S. PATENT DOCUMENTS

| | | | |
|---|---|---|---|
| 4,190,563 A | 2/1980 | Bosley et al. | |
| 4,654,039 A | 3/1987 | Brandt et al. | |
| 4,683,274 A | 7/1987 | Nakamura et al. | |
| 5,145,906 A | 9/1992 | Chambers et al. | |
| 5,300,565 A | 4/1994 | Berg et al. | |
| 5,453,323 A | 9/1995 | Chambers et al. | |
| 5,597,873 A * | 1/1997 | Chambers et al. | 525/330.1 |
| 6,107,432 A * | 8/2000 | Engelhardt et al. | 527/311 |
| 7,285,615 B2 * | 10/2007 | Adachi et al. | 526/319 |
| 2002/0143308 A1 | 10/2002 | Reeves et al. | |
| 2003/0060112 A1 * | 3/2003 | Rezai et al. | 442/340 |
| 2004/0180189 A1 * | 9/2004 | Funk et al. | 428/323 |
| 2005/0031852 A1 | 2/2005 | Schmidt et al. | |
| 2005/0070867 A1 | 3/2005 | Beruda et al. | |
| 2005/0245684 A1 * | 11/2005 | Daniel et al. | 525/178 |
| 2006/0089611 A1 | 4/2006 | Herfert et al. | |

FOREIGN PATENT DOCUMENTS

EP    0 337 976    * 10/1989 .............. C08L 23/08

OTHER PUBLICATIONS

PCT International Search Report dated Jun. 2, 2007.
"Superabsorbent Polymers", Mark Elliott, BASF—The Chemical Company, Mar. 25, 2004, XP002373902.

* cited by examiner

*Primary Examiner* — Michele M Kidwell
(74) *Attorney, Agent, or Firm* — Andres E. Velarde; Amanda T. Barry

(57) ABSTRACT

Absorbent articles for the absorption of proteinaceous or serous body fluids, particularly menses. The absorbent article has a better handling towards such fluids, both in terms of retention capacity and absorption rate, by comprising a selected polyacrylate based material.

11 Claims, No Drawings

ABSORBENT ARTICLE HAVING INCREASED ABSORPTION AND RETENTION CAPACITY FOR PROTEINACEOUS OR SEROUS BODY FLUIDS

FIELD OF THE INVENTION

The present invention relates to absorbent articles for absorption of proteinaceous or serous body fluids, which comprise a polyacrylate based material having an improved capacity of acquiring and retaining such fluids. Particularly the absorbent articles of the present invention comprise sanitary napkins, wherein the body fluid is menses, as well as tampons, interlabial devices, panty liners, wound dressings, breast pads or the like.

BACKGROUND OF THE INVENTION

Absorbent articles for absorption of proteinaceous or serous body fluids such as menses blood, plasma, vaginal secretions, mucus or milk are well known in the art, and typically comprise feminine hygiene articles such as sanitary napkins, panty liners, tampons, and interlabial devices, as well as wound dressings, breast pads or the like. The purpose of such articles is to absorb and retain said body fluids. When considering in particular sanitary napkins and pantiliners, these articles typically comprise a liquid-pervious topsheet as wearer-facing layer, a liquid-impervious backsheet as garment-facing layer and an absorbent core between topsheet and backsheet. The body fluids are acquired through the topsheet and subsequently stored in the absorbent core. The backsheet prevents the absorbed fluids from wetting the wearer's garment.

It is also widely known in the art that it is beneficial for the absorption and retention characteristics of absorbent articles when portions of the article, typically the absorbent core, comprise superabsorbent materials, such as absorbent gelling materials (AGM), usually in finely dispersed form, e.g. typically in particulate form. Conventional superabsorbent materials known in the art for use in absorbent articles typically comprise water-insoluble, water-swellable, hydrogel-forming crosslinked absorbent polymers which are capable of absorbing large quantities of liquids and of retaining such absorbed liquids under moderate pressure. In general, absorbent articles comprising conventional absorbent gelling materials commonly have good absorption and retention characteristics to water and urine; however, there still remains room for improvement for absorption and retention towards certain liquids. In particular, proteinaceous or serous body fluids such as typically menses, blood, plasma, vaginal secretions, mucus or milk, are particularly difficult to be effectively absorbed and retained into absorbent articles containing conventional superabsorbent materials since said materials do not show enough absorption and retention characteristics towards said proteinaceous or serous body fluids.

Such not optimal absorption and retention are mainly caused by poor permeability of conventional superabsorbent materials towards such proteinaceous or serous body fluids, in turn due to the viscosity and/or to the complex nature of the fluids. For example, plasma, blood and menses components, including red cells, white cells, soluble proteins, cellular debris and mucus, slow down the absorption of these fluids by conventional superabsorbents. Because these fluids comprise many complex components, and are often typically rather thick, absorption into conventional superabsorbent polymers is difficult. This translates into a slower initial uptake rate of the fluid into the superabsorbent material, which can result in a lower final absorption and retention capacity if gel blocking occurs before the superabsorbent material is fully swollen.

Attempts to increase the absorption and retention capacity of superabsorbent materials for proteinaceous or serous fluids, such as blood or menses, have led for example to chemical modification of these superabsorbent materials, such as by differential crosslinking between surface and bulk of the particle, or treatment with additives, for example to improve wettability with blood by surface treatment of particulate absorbent materials using particular compounds, as disclosed in U.S. Pat. No. 4,190,563. Alternatively, or in combination, morphological modifications of the superabsorbent materials are also known in the art, for example adopting preferred shapes or dimensions for the particles.

However, although such known approaches have achieved some success in absorption and retention of proteinaceous or serous body fluids by absorbent articles comprising superabsorbent materials, they are associated to several undesirable processing and consumer use concerns. Provision of chemically and/or morphologically modified superabsorbent materials certainly adds complexity, and cost, to the production process for the manufacture of absorbent articles for absorption of proteinaceous or serous body fluids. Moreover, chemically modified superabsorbent materials can loose effectiveness during use, for example a surface coated additive can be washed away from the superabsorbent material by succeeding applications of fluid.

Consequently, there remains a need for further improvements in absorbent articles for absorption of proteinaceous or serous body fluids, such as for example sanitary napkins, which comprise polymeric materials typically in particulate form and have increased fluid absorption and retention capacity, particularly a high intake rate for such body fluids. Additionally, it would be beneficial if a reduced amount of polymeric material as compared to conventional products could be used to achieve said results.

SUMMARY OF THE INVENTION

An absorbent article for absorption of proteinaceous or serous body fluids, which comprises a polyacrylate based material having an extractable fraction of at least about 30% by weight, evaluated according to the Extractables test method described herein.

DETAILED DESCRIPTION OF THE INVENTION

The term "absorbent article" is used herein as including any article able to receive and/or absorb and/or contain and/or retain proteinaceous or serous body fluids. "Absorbent articles" as referred to herein can include, without being limited to, feminine hygiene articles such as sanitary napkins, panty liners, tampons, interlabial devices, as well as wound dressings, breast pads and the like. Particularly, the disposable absorbent article is described below by reference to a sanitary napkin.

The term "disposable" is used herein to describe articles that are not intended to be laundered or otherwise restored or reused as an article (i.e., they are intended to be discarded after a single use and, preferably, to be recycled, composted or otherwise disposed of in an environmentally compatible manner).

As used herein, the term 'wearer-facing', or alternatively 'body-facing', surface refers to the surface of the component of the article generally oriented to face the wearer skin and/or mucosal surface during use of the article. As used herein, the term 'garment facing' surface refers to the opposite outer surface of the article, typically the surface directly facing the garment of a wearer, if worn in direct contact with a garment.

As used herein, the term 'proteinaceous or serous body fluids' refers to bodily fluids secreted by the body which comprise several components and typically have a viscosity higher than urine or water. Some proteinaceous or serous body fluids include for example menses, blood, plasma, vaginal secretions, and also mucus or milk.

In the following, non-limiting embodiment of the present invention, a sanitary napkin is described as an exemplary absorbent article, typically comprising as main elements: a topsheet, facing the user of the article during use and being liquid pervious in order to allow liquids, particularly body fluids, to pass into the article; a backsheet, providing liquid containment such that absorbed liquid does not leak through the article, this backsheet conventionally providing the garment facing surface of the article; and an absorbent core comprised between the topsheet and the backsheet and providing the absorbent capacity of the article to acquire and retain liquid which has entered the article through the topsheet. Of course, other types of absorbent articles according to alternative embodiments of the present invention may not comprise one or more of the above elements, such as for example tampons or wound dressings which typically do not have a backsheet, as can be readily determined by the man skilled in the art. All absorbent articles of the present invention however have an absorbent core, which can be any absorbent means provided in the article and which is capable of absorbing and retaining proteinaceous or serous body fluids, such as for example menses.

The elements constituting the absorbent article of the present invention may be conventional, as it is known in the art and described hereinafter with reference to a sanitary napkin.

Topsheet

The topsheet is compliant, soft feeling, and non-irritating to the wearer's skin. The topsheet also can be elastically stretchable in one or two directions. Further, the topsheet is liquid pervious permitting body fluids to readily penetrate through its thickness.

A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims.

Backsheet

The backsheet prevents the liquids absorbed and contained in the absorbent element from wetting articles that contact the absorbent article such as pants, pajamas and undergarments. The backsheet can be typically impervious to liquids like body fluids and can be manufactured from a thin plastic film, although other flexible liquid impervious materials can also be used. The backsheet can also be optionally breathable, thus permitting the transfer of water vapor and preferably both water vapor and air through it and thus allows reduction of humid and occlusive environment on the skin contacted with the article.

Absorbent Core

The absorbent core, which is disposed between the topsheet and the backsheet, absorbs and retains bodily fluids that have penetrated the topsheet after discharge by a wearer. The absorbent core may be any absorbent means which is capable of absorbing or retaining bodily liquids (typically menses for a sanitary napkin). The absorbent core may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges.

Polyacrylate Based Material.

According to the present invention, the absorbent article for absorption of proteinaceous or serous body fluids also comprises a polyacrylate based material which has an improved absorption and retention capacity towards such proteinaceous or serous body fluids, particularly towards menses.

The polyacrylate based materials incorporated in the absorbent articles of the present invention are polyelectrolytes with a multiplicity of anionic functional groups, typically carboxyl groups. In preferred embodiments, the polyacrylate based materials can comprise polyacrylates, polymethacrylates, and derivatives thereof, such as for example polyacrylate sodium, polymethacrylate sodium, polyacrylate potassium, polymethacrylate potassium, starch grafted polyacrylate, starch grafted polymethacrylate, polyvinyl alcohol grafted polyacrylate, polyvinyl alcohol grafted polymethacrylate, cellulose grafted polyacrylate, cellulose grafted polymethacrylate, and the like.

As it is known in the art, the polyelectrolytes which provide the polyacrylate based materials incorporated in the absorbent articles of the present invention can be made from polymerizable, unsaturated, acid-containing monomers. Such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof.

Polyacrylate based materials, typically partially neutralized polymers, are commonly incorporated in absorbent articles and are known as superabsorbent polymers (SAP), or superabsorbents, and are crosslinked. According to the well known mechanism, the polyacrylate material has neutralized, typically with sodium, carboxylate groups hanging off the main polymer chain. In contact with water the sodium detaches and goes in solution, leaving only carboxyl ions. Being negatively charged, these ions repel one another so that the polymer unwinds and absorbs more and more water, which is instead attracted by the carboxyl ions, as further carboxyl ions become available. The hydrogen in water is trapped by the polyacrylate due to the atomic bonds associated with the polarity forces between the atoms. The crosslinks, which bridge different polymer chains, lead to a three dimensional structure, which upon liquid absorption constitutes the swollen gel.

According to the present invention, it has been surprisingly discovered that polyacrylate based materials being very slightly crosslinked, or substantially not crosslinked at all, incorporated in absorbent articles for the absorption of proteinaceous or serous body fluids such as for example menses, blood, plasma, vaginal secretions, and also mucus or milk, but particularly menses, can provide an improved absorption and retention capacity for such body fluids, and an improved absorption rate as well, compared to traditional crosslinked superabsorbents.

Without being bound to any theory, it is believed that slightly crosslinked, or substantially not crosslinked polyacrylate based polymers incorporated in absorbent articles for the absorption of proteinaceous or serous body fluids are capable of easily acquiring and retaining said body fluids containing complex components and being typically rather thick and viscous, owing to their increased permeability to said fluids, which can be then effectively acquired and immobilized into the swollen polymer within the structure of the absorbent article. Reduced crosslinking, or lack of crosslinking at all, are supposed to provide this better permeability towards proteinaceous or serous body fluids, especially towards menses within sanitary absorbent articles such as sanitary napkins.

A measure of the degree of crosslinking of a polyacrylate based polymer can be expressed in terms of the soluble or extractable fraction of the polymer. As it is known in the art, lower molecular weight polymer chains can be solubilized, or extracted, from the polymer in certain conditions, and represent said soluble or extractable fraction of the polymer itself. Generally, the extractable fraction can be considered to be inversely proportional to the degree of crosslinking, that is, the higher the degree of crosslinking, the lower the fraction, since a greater proportion of the polymer mass is actually incorporated into the polymer network. According to the present invention, it has been found that a polyacrylate based polymer to be incorporated in an absorbent article for absorption of proteinaceous or serous body fluids, particularly menses, has an extractable fraction of at least about 30%, preferably of at least about 32%, more preferably of at least about 35% by weight, wherein said extractable fraction is evaluated with the test method described herein. Typically, said extractable fraction should be not more than about 80% by weight of the polyacrylate based material, preferably not more than about 70% by weight.

In an embodiment of the present invention, said extractable fraction can have an average molecular weight of at least about 30,000 Dalton, or even of at least about 100,000 Dalton, or even of at least about 500,000 Dalton, wherein the average molecular weight is evaluated with one of the methods known in the art, for example by means of a Gel Permeation Chromatography method. As known to the skilled person, the extractables can be separated from the polyacrylate based material by selecting a suitable solvent, or eluent, which is compatible with the apparatus for measuring the average molecular weight, as can be readily determined by the man skilled in the art. For example, when the Gel Permeation Chromatography method is selected, a suitable eluent can be a 50:50 water/ethanol solution, which does not cause swelling of the polyacrylate based material, and at the same time does not interfere with the chromatography apparatus. Relatively high average molecular weights of the extractable fraction can be preferred since they correspond to a polyacrylate based polymer overall not containing low and very low molecular weight polymer chains which are easily solubilized also in the relatively thick proteinaceous or serous body fluids, but rather has an extractable fraction which actually contributes to the absorbing and immobilizing action of the polymer towards said fluids.

Crosslinking degree of the polyacrylate based polymers comprised in the absorbent articles of the present invention can also be expressed as percentage of crosslinking agent in the polymer. It is typical that said polyacrylate based polymers comprise an amount of crosslinking polymer of less than about 0.03 mole % with respect to the acrylic acid monomer, or even of less than about 0.005 mole %, or even of less than about 0.001 mole %. In general crosslinking agents for polyacrylate based materials are well known in the art and can typically comprise bifunctional compounds capable of reacting with the polymer chains in order to provide the network crosslinking.

According to the present invention, among polyacrylate based polymers to be incorporated in absorbent articles for the absorption of proteinaceous or serous body fluids, particularly menses, polyacrylates can be actually preferred, particularly polyacrylates neutralized with sodium, potassium or lithium.

Methods for forming the polyacrylate based materials in particle form to be incorporated in the absorbent articles of the present invention can be those involving aqueous solution polymerization methods. The aqueous reaction mixture of monomers is subjected to polymerization conditions, which are sufficient to produce substantially water-insoluble, slightly network crosslinked polyacrylate based material. Crosslinking, when present, can be achieved with known means, e.g. addition of a suitable crosslinking agent in a selected amount in order to obtain a desired low level of crosslinking degree. Neutralization can be typically achieved with reaction with a suitable base, for example NaOH in order to get a sodium neutralized polyacrylate based polymer. The polymer formed, once dried, can then be chopped or ground to form individual particles as it is known in the art.

In addition, the formation process of the polyacrylate based material to be incorporated in an absorbent article of the present invention can also include the provision of a blowing agent, in order to obtain a porous polyacrylate based material, according to one of the methods known in the art.

According to an embodiment of the present invention, an at least partially neutralized polyacrylate based material to be comprised in an absorbent article can be obtainable with a process comprising a neutralization step performed directly on the acid monomers, before the actual polymerization step.

Partially neutralized polyacrylate based polymers, particularly polyacrylates and polymethacrylates, can be preferred for their good fluid absorbency and permeability. A degree of neutralization between about 70% and about 80% can be particularly useful, typically around about 75%. Neutralization degrees above about 80% can provide a faster absorption and swelling which can be generally used in the absorbent articles of the present invention when absorption and swelling rate are particularly desirable in addition to retention capacity. Conversely, a degree of neutralization below about 70% may be also beneficial in that it can confer the polyacrylate based polymer a delayed swelling upon liquid absorption, while keeping a good absorbency and retention capacity. This can be adopted in some embodiments of the present invention where an absorbent article incorporates a rather high amount of the polyacrylate based material; delayed swelling can help efficient liquid acquisition and distribution in combination with still good retention capacity.

Typically, and similarly to the superabsorbent materials commonly comprised in absorbent articles, the polyacrylate based materials comprised in the absorbent articles of the present invention can be in a particulate form wherein particles may be of numerous regular or irregular shapes. The term "particles" refers in fact to granules, beads, flakes, spheres, powders, platelets, fibres and other shapes and forms known to the person skilled in the art of superabsorbent materials. It is typical that the average particle size of the polyacrylate based material in dry state used herein is between about 10μ and about 1,000μ, preferably between about 50μ and about 1,000μ, more preferably between about 100μ and about 800μ, most preferably between about 150μ and about 600μ. Smaller particle sizes within the preferred ranges above can be advantageous as this results in optimum performance. Even smaller particle sizes, e.g. below about 50μ, for example between about 20μ and about 40μ, can be also used in absorbent articles of the present invention as they can be beneficial for fluid handling capability, wherein particles of such a small size have to be effectively and stably contained within the structure of the absorbent article. "Particle size" as used herein means the weighted average of the smallest dimension of the individual particles.

The polyacrylate based materials to be incorporated in the absorbent articles of the present invention show improved retention capacity and permeability towards proteinaceous or serous body fluids. Said polyacrylate based materials can typically have a retention capacity towards Artificial Menses Fluid (AMF), evaluated according to the Centrifuge Retention Capacity (CRC) test method described herein, of at least about 30 g/g, preferably of at least about 35 g/g, more preferably of at least about 40 g/g.

In an embodiment, the polyacrylate based materials comprised in the absorbent articles of the present invention can have an absorption rate towards AMF of at least about 24 g/g after 30 min, preferably of at least about 28 g/g after 30 min, evaluated with the same CRC test method mentioned above.

The polyacrylate based materials can be incorporated in the absorbent articles of the present invention typically in the absorbent core, in different embodiments as it is known in the art. The absorbent core can comprise the polyacrylate based material in particle form dispersed within its structure, for example uniformly or non-uniformly mixed with absorbent fibres, such as cellulose or fluff pulp. Alternatively, the polyacrylate based materials in particle form can be comprised in layered core structures or also laminated core structures with outer fibrous layers and particles of the polyacrylate based material comprised therebetween, or composite structures comprising any of the above structures and one or more further layers below or above it, e.g. fibrous layers such as for example spunlaced nonwoven layers.

In certain embodiments, the polyacrylate based materials typically in particle form can be present in an absorbent article according to the invention, typically in its absorbent core, with a basis weight of from about 5 g/m² to about 500 g/m², preferably from about 10 g/m² to about 100 g/m², more preferably from about 20 g/m² to about 60 g/m², most preferably from about 25 g/m² to about 40 g/m².

Typically, the absorbent core of the absorbent article of the present invention can include from about 1% to about 90% by weight of the polyacrylate based material, preferably from about 5% to about 50% by weight, more preferably from about 10% to about 30% by weight.

The invention will be illustrated with the following examples.

Example 1

A sanitary napkin comprises, from top to bottom, as the topsheet an apertured polymeric film (CPM RIS coded 1035025 available from Tredegar), as the fluid acquisition/distribution layer a 40 g/m² BICO thermalbonded carded nonwoven (coded Sawabond 4313 available from Sandler), as the absorbent core a composite air laid structure comprising bicomponent and cellulose fibres, superabsorbent particles, and a binder, as sold by Concert GmbH under the code GH.150.1006, and as the backsheet a polyethylene film manufactured by Clopay Corporation of Cincinnati, Ohio, under the designation P18-0401.

The superabsorbent particles comprised in the absorbent core are available from Degussa AG under the trade name Favor® Z 3070 and have a particle size comprised between 150μ and 600μ.

Example 2

A sanitary napkin as that of Example 1, wherein the commercial superabsorbent particles are replaced by a very slightly crosslinked polyacrylate material in particle form having the same particle size of 150-600μ. The polyacrylate based material is synthesized from acrylic acid monomers neutralized with NaOH and then polymerized and very slightly crosslinked according to the following procedure.

To 300 g of glacial acrylic acid, 0.18 g of MethyleneBisAcrylAmide (MBAA) are added and allowed to dissolve at ambient temperature. A 2500 ml resin kettle (equipped with a four-necked glass cover closed with septa, suited for the introduction of a thermometer, syringe needles, and optionally a mechanical stirrer) is charged with this acrylic acid/crosslinker solution. The mixture is kept under stirring with a magnetic stirrer. 83.26 g of 50% NaOH solution (the amount of NaOH needed to neutralize 75% of the acid groups of the polymer) are diluted with distilled water (kept at 0-5° C.) to 1166.8 g (the concentration of acrylic acid is 20% by weight). Most of the solution is added to the resin kettle, and the mixture is stirred until the monomer and NaOH solution are well mixed. 300 mg of an initiator ("V50" from Waco Chemicals) are dissolved in 20 ml of deionized water. Then, the initiator solution is added together with any remaining water. The resin kettle is closed, and a pressure relief is provided e.g. by puncturing two syringe needles through the septa. The solution is then purged vigorously with argon via an 80 cm injection needle while stirring at approx. 300 rpm. Stirring is discontinued after approx. 8 minutes, while argon purging is continued. The solution typically starts to gel after 12-20 minutes. At this point, persistent bubbles form on the surface of the gel, and the argon injection needle is raised above the surface of the gel. Purging with argon is continued at a lowered flow rate. The temperature is monitored, typically it rises from 20° C. to 60-70° C. within one hour. Once the temperature drops below 60° C., the kettle is transferred into a circulation oven and kept at 60° C. for 15-18 hours. After this time, the resin kettle is allowed to cool, and the resulting gel is removed into a flat glass dish. The gel is then broken or cut with scissors into small pieces (for example in pieces smaller than 2 mm max. dimension), and transferred into a 6 l glass beaker. Then, it is covered and transferred into a 60° C. oven and let equilibrate for 1 day. After this time, the gel is allowed to cool, then divided up into 2 flat glass dishes, and transferred into a vacuum oven, where it is dried at 40° C. max. Once the gel has reached a constant weight (usually after 3 days), it is ground using a mechanical mill (e.g. IKA mill) and sieved to obtain SAP particles of the required particle size, e.g. between 150μ and 600μ. If not otherwise stated, all compounds were obtained from Aldrich Chemicals, Milwaukee, Wis., USA.

The values of the extractable fraction, absorption rate and retention capacity of the superabsorbent material of Example 1 and of the polyacrylate based material of Example 2 are summarized in the following table:

|  | Extractable fraction (% by weight) | Absorption rate (g/g) | Retention capacity (g/g) |
| --- | --- | --- | --- |
| Favor ® Z 3070 | 10.9 | 21.7 | 26.6 |
| Polyacrylate based material of Ex. 2 | 30.4 | 24.3 | 35.5 |

The polyacrylate based material has a much higher retention capacity for AMF compared to the commercial SAP, and a higher absorption rate, and provides a sanitary napkin for absorption of menses with a greatly increased absorption and retention capacity towards a body fluid having a complex nature such as menses. Surprisingly, the sanitary napkin of this preferred embodiment of the present invention is capable of acquiring larger amounts of menses, and of effectively immobilizing it in its structure, by including a polyacrylate based material which is not recognized as suitable for absorption of liquids, and which is simple to produce and to handle. According to the present invention, it is also possible to obtain an absorbent article, for example a sanitary napkin, which provides substantially the same liquid handling capability, in terms of retention capacity and absorption rate, of a known similar absorbent article comprising a traditional superabsorbent material, with a sensibly lesser amount of the selected polyacrylate based material, with clear advantages in terms of processability, manufacture and cost.

Test Procedures.

Centrifuge Retention Capacity Test.

The test is based on the Edana Recommended Test Method 441.2-02 (Centrifuge Retention Capacity), with the following changes which refer to the corresponding sections and subsections of the test method description:

Section 1—Scope

The present method determines the fluid retention capacity of polyacrylate polymers (commercial superabsorbent polymers and polyacrylate based polymers according to the present invention) in Artificial Menstrual Fluid (AMF) following centrifugation.

Section 6—Reagents

Only AMF is used.

Section 7—Apparatus 7.6 A timer accurate to 1 s over 4 hours is used.

7.3 The large pan is replaced by a beaker, of 600 ml capacity and 95 mm inner diameter. In addition a plastic screen support is needed, for example a plastic net with square pattern and about 5 mm mesh, cut in square shape with the same dimension as the nonwoven bag under 7.1, and with a handle e.g. constituted by a metal wire, inverted-U shaped and fixed to two opposite sides of the plastic screen support, in order to introduce the plastic screen support with the bag into the 600 ml beaker, and to subsequently withdraw it as described in modified 9.3 below.

7.7 No volumetric flask is needed.

Section 9—Procedure 9.6 Fill the 600 ml beaker with 200 ml of AMF. Change the AMF after a maximum of four bags.

9.8 The bag is placed flat on the plastic screen support, which is then immersed in the AMF within the beaker by means of the handle. Allow the bag to become wet for one minute before pushing it under the liquid surface if necessary. Eliminate entrapped air bubbles by manipulating the bag.

9.9 After the selected time, take out the plastic screen support with the bag from the AMF. The procedure has to be repeated for the following times: 30 and 240 minutes.

As also mentioned in the original test method under 9.5, the test on the blanks need not be carried out if same conditions apply.

Section 10—Calculation

For each time (30 and 240 minutes) the test is run on four sample replicates, instead of two as prescribed in the original test method, and the result is taken as the average of the four calculated values.

The value of the Centrifuge Retention Capacity after 240 minutes is taken as the retention capacity of the polyacrylate based material according to the invention. The value of the Centrifuge Retention Capacity after 30 minutes is taken as the absorption rate of the polyacrylate based material.

Extractables Test.

The test is based on the Edana Recommended Test Method 470.2-02 (Extractables), with the following changes and specifications which refer to the corresponding sections and subsections of the test method description:

Section 6—Reagents 6.5 The software of the pH meter allows the use of standard buffer solutions pH 4 and pH 7 (see note at 7.2 below).

Section 7—Apparatus 7.2 The pH meter with combined glass pH-responsive electrode is a Hanna mod. pH213 microprocessor.

7.11 Selected filter papers are Schleicher & Schuell 597, 100 mm in diameter, with a pore size from 4µ to 7µ.

7.14 An orbital stirrer at 450 rpm has been used.

Artificial Menstrual Fluid (AMF)

Artificial Menstrual Fluid is based on modified sheep's blood that has been modified to ensure it closely resembles human menstrual fluid in viscosity, electrical conductivity, surface tension and appearance. It is prepared as explained in U.S. Pat. No. 6,417,424, assigned to The Procter & Gamble Company, from line 33 of column 17 to line 45 of column 18, to which reference is made.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for absorption of proteinaceous or serous body fluids, comprising a polyacrylate based material synthesized from acrylic acid monomers, the polyacrylate based material comprising a polyacrylate or a polymethacrylate and having an extractable fraction of the polyacrylate or the polymethacrylate of between 32% and 80% by weight, evaluated according to the Extractables test method described herein, wherein said extractable fraction has an average molecular weight of at least 30,000 Dalton, wherein the average molecular weight of the extractable fraction comprises polyacrylates, and wherein said polyacrylate based material has a retention capacity of at least 30 g/g, said retention capacity evaluated according to the Centrifuge Retention Capacity test described herein.

2. An absorbent article according to claim 1, wherein said polyacrylate based material has an extractable fraction between 35% and 70% by weight.

3. An absorbent article according to claim 1, wherein said polyacrylate based material is a particulate material with an average particle size between 10μ and 1,000μ.

4. An absorbent article according to claim 1, wherein said polyacrylate based material comprises an amount of crosslinking agent of less than 0.03 mole %.

5. An absorbent article according to claim 1, wherein said polyacrylate based material has a degree of neutralization between 70% and 80%.

6. An absorbent article according to claim 1, wherein said polyacrylate based material has a degree of neutralization of at least 75%.

7. An absorbent article according to claim 1, wherein said polyacrylate based material has a degree of neutralization below 70%.

8. An absorbent article according to claim 1, wherein said polyacrylate based material is a sodium polyacrylate.

9. An absorbent article according to claim 1, wherein said article comprises a topsheet, a backsheet and an absorbent core, said polyacrylate based material being comprised in said absorbent core.

10. An absorbent article according to claim 9, wherein said absorbent core comprises from 1% to 90% by weight of said polyacrylate based material.

11. An absorbent article according to claim 1, wherein said polyacrylate based polymer is at least partially neutralized, and is obtainable with a process comprising a neutralization step performed directly on the acid monomers, before the actual polymerization step.

* * * * *